United States Patent
Legard et al.

(10) Patent No.: US 7,308,068 B2
(45) Date of Patent: Dec. 11, 2007

(54) DEVICE AND METHOD FOR CONTROLLING THE EXTERIOR ASPECT OF FUEL RODS FOR NUCLEAR REACTORS

(75) Inventors: Patrick Legard, Houilles (FR); Serge Fantini, Orange (FR)

(73) Assignee: Compagnie Generale des Matieres Nucleaires, Velizy-Villacoublay (FR)

( * ) Notice: Subject to any disclaimer, the term of this patent is extended or adjusted under 35 U.S.C. 154(b) by 0 days.

(21) Appl. No.: 10/883,877

(22) Filed: Jul. 2, 2004

(65) Prior Publication Data

US 2005/0011929 A1    Jan. 20, 2005

(30) Foreign Application Priority Data

Jul. 4, 2003   (FR) .................................. 03 50294

(51) Int. Cl.
    *G21C 17/00*   (2006.01)
(52) U.S. Cl. ..................... 376/248; 376/245; 376/258; 356/237.1
(58) Field of Classification Search ................ 376/248, 376/245, 228, 258; 356/237.1
    See application file for complete search history.

(56) References Cited

U.S. PATENT DOCUMENTS

| | | | | |
|---|---|---|---|---|
| 4,255,762 A | * | 3/1981 | Takeyasu et al. | 348/84 |
| 4,464,332 A | * | 8/1984 | Boisseuil et al. | 376/215 |
| 4,605,531 A | * | 8/1986 | Leseur et al. | 376/252 |
| 4,649,650 A | * | 3/1987 | Fink et al. | 33/783 |
| 4,657,728 A | * | 4/1987 | Coppa et al. | 376/248 |
| 5,215,706 A | * | 6/1993 | Cross et al. | 376/252 |
| 5,305,356 A | * | 4/1994 | Brooks et al. | 376/249 |
| 6,145,583 A | * | 11/2000 | Gay et al. | 165/11.2 |
| 6,549,600 B1 | * | 4/2003 | Beier et al. | 376/258 |
| 6,879,653 B2 | * | 4/2005 | Arias et al. | 376/252 |
| 2001/0019596 A1 | * | 9/2001 | Arias et al. | 376/245 |
| 2002/0075984 A1 | * | 6/2002 | Knecht et al. | 376/253 |
| 2004/0032924 A1 | * | 2/2004 | Judge, Jr. | 376/268 |

FOREIGN PATENT DOCUMENTS

| | | | | |
|---|---|---|---|---|
| GB | 1108235 | | 4/1968 | |
| GB | 2 036 375 A | | 6/1980 | |
| WO | WO 01/11632 A1 | * | 2/2001 | 376/248 |

OTHER PUBLICATIONS

Japan Patent Abstracts, Kubo Katsumi, "Determining Apparatus for Surface Flaw of Nuclear Fuel Cladding Tube", Publication No. 04115192, Publication date: Apr. 16, 1992, 1 page.

Japan Patent Abstracts, Wada Takashi, "Surface Flaw Detecting Method of Nuclear Fuel Coated Tube", Publication No. 10078413, Publication Date: Mar. 24, 2003, 1 page.

Japan Patent Abstracts, Nagao Tetsuya, "Groove Part Testing Device", Publication No. 11014343, Publication Date: Jan. 22, 1999, 1 page.

* cited by examiner

*Primary Examiner*—Ricardo J. Palabrica
(74) *Attorney, Agent, or Firm*—Pearne & Gordon LLP

(57) ABSTRACT

The invention concerns a device (1) for controlling the exterior aspect of fuel rods (2) for nuclear reactors, said device comprising optical means (40) having at least one camera (42, 42') and linked to an image acquisition and processing system (48) capable of detecting geometric defects present on each rod (2) to be controlled, and further comprising a roughness tester (50) controlled in such a way as to measure the depth of each geometric defect detected by the image acquisition and processing system (48).

Moreover, the invention further concerns a method capable of being implemented with the aid of said device (1).

9 Claims, 4 Drawing Sheets

DEVICE AND METHOD FOR CONTROLLING THE EXTERIOR ASPECT OF FUEL RODS FOR NUCLEAR REACTORS

TECHNICAL FIELD

The present invention concerns, in a general manner, the field of controlling the exterior aspect of fuel rods for nuclear reactors and, more specifically, the field of devices and methods for controlling the exterior aspect of fuel rods at the end of the production cycle.

STATE OF THE PRIOR ART

Typically, fuel rods for nuclear reactors are zirconium alloy claddings in which are placed fissile materials. This type of cladding, generally having a length between 3 and 5 metres and a diameter between 8 and 15 mm, have a first sealed end and a second open end, said second end being sealed by means of a cap welded onto the cladding, after the introduction of the fissile materials into the interior of said cladding.

At the end of the production of a fuel rod, it is normally necessary for its exterior surface, overall cylindrical and of circular section, to have a satisfactory surface condition, for example of the "polished mirror" type.

Thus, in order to control the exterior aspect of a rod when it leaves production, a detection is carried out for several types of defects over the whole of the exterior surface of the rod including, notably, the exterior surface of the end cap.

Among the defects searched for, in first place are geometric defects, which may be assimilated to three dimensional defects present on the exterior surface of the rod.

By way of illustrative examples, the geometric defects may take the form of longitudinal or circumferential grooves on the exterior surface of the rod, whereby said grooves may be considered as defects when they attain a depth greater than 25μ. Moreover, the defects may also take the form of impacts, caulking or even stripping off of material, still on the said exterior surface of the rod.

The control of the exterior aspect of a fuel rod further consists in detecting cleanliness defects, said defects generally being in the form of traces of oil or foreign bodies on the exterior surface, or even in the form of black or coloured marks with a surface area greater than a determined value.

Finally, a third category of defect to be detected concerns apparent defects in the end cap weld. Said type of defect, which may be present on the weld bead of said end cap, may be in the form of pitting, blisters, cracking, overflows, shortages, sags or even colouring defects in the weld bead.

A solution is known from the prior art that aims to control the exterior aspect of fuel rods at the end of production, through the intermediary of a qualified operator working with the naked eye and without any measurement tool at his disposal.

Indeed, the fuel rods at the end of production are typically arranged horizontally on a stand, in bundles of thirty two elements. Once installed, they are then capable of being rotated around their own axes longitudinally by means of a friction drive mechanism, so that the operator can control all of the exterior surfaces of said rods. In this respect, it is noted that tangential lighting, which may be intensity adjusted, facilitates the detection of defects by the qualified operator.

However, during exterior aspect control operations, a lead glass screen must be provided between the rods and the operator, with the obvious aim of protecting said operator against the irradiation emitted by the fuel rods. Accordingly, a major disadvantage relating to the presence of the screen is that it has a thickness of around 100 mm and that, consequently, it is not completely translucent. Moreover, an increase in the extent of scratching on said screen over time considerably restricts the operator's view.

Under these conditions, the evaluation of certain defects such as the surface area of stains, the depth of grooves or even the evaluation of the colouring of weld beads becomes relatively difficult to perform. Thus, if the operator has any doubts, the rod in question is put aside in order to be recontrolled by another operator, which results directly in a significant waste of time and a not insignificant increase in the cost of producing the rods.

It is also pointed out that the implementation of this exterior aspect control technique has disadvantages directly linked to the presence of the operator not equipped with measurements means.

In effect, in the case of defects for which the size, depth or colouring needs to be evaluated, the resulting verdict is, to a great extent, determined by the experience and tiredness of the operator, his tiredness nevertheless being increased by the wearing of protective lead apron and the extreme and permanent attention that this type of control station requires. Consequently, particularly when a geometric defect has been detected by the operator but his assessment of the depth is mistaken, said operator may be induced to make a false reject or, quite the reverse, not take into consideration a defect that is, however, not acceptable.

Finally, it is pointed out that production objectives generally require a large number of operators qualified in the field of controlling the exterior aspect of fuel rods, which naturally leads to high production costs.

OBJECTS OF THE INVENTION

The aim of the invention is therefore to propose a device and a method for controlling the exterior aspect of fuel rods for nuclear reactors, which at least partially overcomes the above mentioned disadvantages in respect of the prior art.

More specifically, the aim of the invention is to present a device and a method for controlling the exterior aspect of fuel rods using an appropriate tooling that makes it possible to produce a reliable, exact and repetitive verdict over time for at least part of the above mentioned defects, contrary to the solution proposed by the prior art in which the human verdict is subject to interpretation and risks leading to false rejects and/or absences of detection of defects that really degrade the exterior aspect of the rod.

In order to achieve this, a first object of the invention is a device for controlling the exterior aspect of fuel rods for nuclear reactors, comprising optical means having at least one camera and linked to an image acquisition and processing system capable of detecting geometric defects present on each rod to be controlled, and further comprising a roughness tester controlled in such a way as to measure the depth of each geometric defect detected by the image acquisition and processing system.

Advantageously, with the control device according to the invention, the detection of geometric defects such as those described previously is no longer carried out by means of the human eye, but automatically, through the intermediary of optical means such as cameras, coupled to an image acquisition and processing system capable of detecting said type of defects. When a geometric defect has been detected by the image acquisition and processing system, the roughness tester is then controlled in such a way that it can measure the depth of said defect, for example with the aim of comparing it to a pre-established value in order to determine if the defect is acceptable or not.

Thus, the problems encountered in the prior art, linked to the fatigue and assessment of the operator, are totally removed, not just in the work of detecting geometric defects present on the rods but also in the operation of evaluating the depth of said defects. Consequently, the risks of false rejects of fuel rods are practically reduced to zero, which is directly reflected by savings in terms of production costs and control times.

Advantageously, it is pointed out that the optical means are capable of scanning the exterior surface of a rod without there being any protective lead glass screen located between the two entities. In this way, the device according to the invention is capable of detecting geometric defects of very small size, even those that are difficult to see with the naked eye.

Furthermore, the conventional processing electronics required for the proper operation of the device can easily be moved from the sensitive zone, in such a way that it is consequently not subjected to the irradiations emitted by the fuel rods.

Moreover, the control device according to the invention, preferably intended to control the exterior aspect of rods at the end of the production cycle, is capable of operating continuously, without requiring qualified operators.

Again advantageously, the presence of the optical means and the roughness tester near to the fuel rods only takes up very little space.

In this respect, it is pointed out that the measurement precision capable of being procured by a conventional roughness tester, for example an optical roughness tester, is completely adapted to that required for the present needs. Moreover, said measurement devices advantageously do not require contact with the rod to carry out the measurements of the depths of the geometric defects, nor even the presence of hydrogenated material between said measurement device and the rod, said configuration being in any case totally excluded for obvious reasons of safety/criticity.

Furthermore, it is pointed out that the device according to the invention may advantageously employ the optical means and the image acquisition and processing system in order to detect other types of defects than geometric defects. Indeed, the image acquisition and processing system is of the two dimension processing software type, and is therefore perfectly capable of detecting all cleanliness defects such as the presence of traces of oil and foreign bodies on the exterior surface of a rod, or even the presence on said same surface of black or coloured marks of surface areas greater than a determined value.

In the same way, the system is also capable of detecting all of the aspect defects of the end cap weld, such as pitting, blisters, cracking, overflows, shortages, sags or even colouring defects in the weld bead.

Preferentially, the control device comprises:
a displacement stand on which may be placed a platform equipped with a plurality of fuel rods arranged substantially parallel alongside each other, said platform being arranged on the stand in such a way that the rods are laid out parallel to a longitudinal direction of said stand,
a trolley capable of being displaced parallel to the longitudinal direction of said displacement stand,
an inspection and measurement head support mounted on the trolley and capable of being displaced in relation to said trolley parallel to a transversal direction of said displacement stand,
an inspection and measurement head comprising at least the optical means and the roughness tester,
means of rotating the fuel rods, capable of rotating each of the rods along their own longitudinal axes,
an electronic and computer assembly comprising notably said image acquisition and processing system, and
a coding ruler provided on the displacement stand and capable of delivering, to the electronic and computer assembly, the position of the trolley in relation to said stand.

Advantageously, this specific arrangement makes it possible to control a plurality of rods placed, for example, in bundles and horizontally and for this to be done automatically by means of the electronic and computer assembly that is preferentially provided so as to be able to control all of the displacements and the actions of the various elements making up the device. In this respect, it is notably pointed out that the presence of the coding ruler on the displacement stand makes it possible to perfectly locate the detected defects, this then allowing precise displacements and positioning of the roughness tester, so that said roughness tester can measure the depths of the different geometric defects detected.

Preferably, for each rod, the optical means are capable of carrying out a scan of the exterior surface of the rod by a plurality of displacements of the trolley along the length of the rod concerned, each displacement being carried out for a given angular position of the rod. Consequently, by judiciously adjusting the various angular positions of the rod concerned, it is easily possible to scan the whole of the exterior surface of said rod by carrying out several backward and forward movements with the trolley, each backward and forward movement then being intended for the inspection of a specific angular section of said exterior surface.

Moreover, one can provide that, during a scan of the exterior surface of a rod, the optical means are capable of delivering a plurality of images to the image acquisition and processing system, each image delivered from the rod being associated with an address indicating the angular position of said rod and the position of the trolley in relation to the displacement stand.

Preferably, as mentioned previously, when at least one geometric defect has been detected on a rod by the image acquisition and processing system, the electronic and computer assembly is capable of provoking, thanks to the addresses associated with the images delivered by the optical means, the displacement of the roughness tester in such a way that it can measure the depth of each geometric defect detected.

The optical means preferably comprise a plurality of primary cameras and a plurality of secondary cameras, said primary and secondary cameras being charge coupled devices (CCD cameras) and each being capable of simultaneously scanning at least two adjacent fuel rods.

Again in a preferred manner, the primary cameras and the secondary cameras are mounted on a plate assembled on the inspection and measurement head support, and the secondary cameras are arranged in such a way as to be able to scan a truncated surface of an end cap of each of the fuel rods to be controlled, when said rods are rotated.

Moreover, the roughness tester is preferentially mounted on a lifting plate assembled on the inspection and measurement head support in such a way that the roughness tester can be brought closer to each rod to carry out the measurement of the depth of each geometric defect detected.

In a preferred embodiment of the present invention, the inspection and measurement head further comprises diode detectors and lighting ramps that make it possible to detect cleanliness defects, such as traces of oil, present on each fuel rod to be controlled. Consequently, said diode detectors can, if necessary, be used to detect traces of oil that are difficult to detect with the aid of the previously described optical means and coupled to the image acquisition and processing system.

Naturally, the association between the diode detectors and the lighting ramps could also be used to assure the detection of any other element likely to substantially modify the light reflection produced by the rods concerned.

Finally, one can provide that the electronic and computer assembly comprises information means capable of delivering and/or memory storing, for each rod controlled, a result file of the control-carried out. By way of indicative examples, this result file may, for example, indicate "pass", "fail" or "to be recontrolled", as well as the address and/or image of the defect(s) detected in the two latter cases.

A further object of the invention is a method for controlling the exterior aspect of fuel rods for nuclear reactors, comprising the following steps:

detection of geometric defects present on each rod to be controlled, with the aid of optical means having at least one camera and linked to an image acquisition and processing system, and measurement of the depth of each geometric defect detected during the detection of geometric defects step, with the aid of a roughness tester.

Preferentially, for each rod, the geometric defect detection step comprises a scanning operation of the exterior surface of the rod with the aid of the optical means, the scanning operation being carried out by a plurality of displacements of the optical means along the length of the rod concerned, each displacement being carried out for a given angular position of each rod.

During the scanning operation of the exterior surface of a rod, the optical means preferably deliver a plurality of images to the image acquisition and processing system, each image delivered from the rod being associated with an address indicating the angular position of said rod and the position of a trolley on which are mounted the optical means, in relation to a displacement stand.

Preferably, when at least one geometric defect has been detected on a rod by the image acquisition and processing system, a displacement of the roughness tester is carried out, thanks to the addresses associated with the images delivered by the optical means, in such a way that it can measure the depth of each geometric defect detected.

Preferably, the measurement of the depth of each geometric defect detected is carried out by bringing closer the roughness tester to the rod concerned.

Furthermore, one can provide that the scanning operation of the exterior surface of the rods is carried out by means of a plurality of primary cameras and a plurality of secondary cameras, said primary and secondary cameras being cameras with a charge coupled device, and each simultaneously scanning at least two adjacent fuel rods.

In a preferred embodiment of the present invention, the control method further comprises an operation of detecting cleanliness defects present on each fuel rod to be controlled, such as traces of oil, the operation being carried out by means of diode detectors and lighting ramps.

Finally, the method preferably comprises a delivery step, for each rod controlled, of a result file of the control carried out.

Other advantages and characteristics of the invention will become clearer on reading the non-limitative description that follows.

BRIEF DESCRIPTION OF THE DRAWINGS

This description will be made with respect to the appended drawings, among which.

DETAILED DESCRIPTION OF PREFERRED EMBODIMENTS

Figure 1:
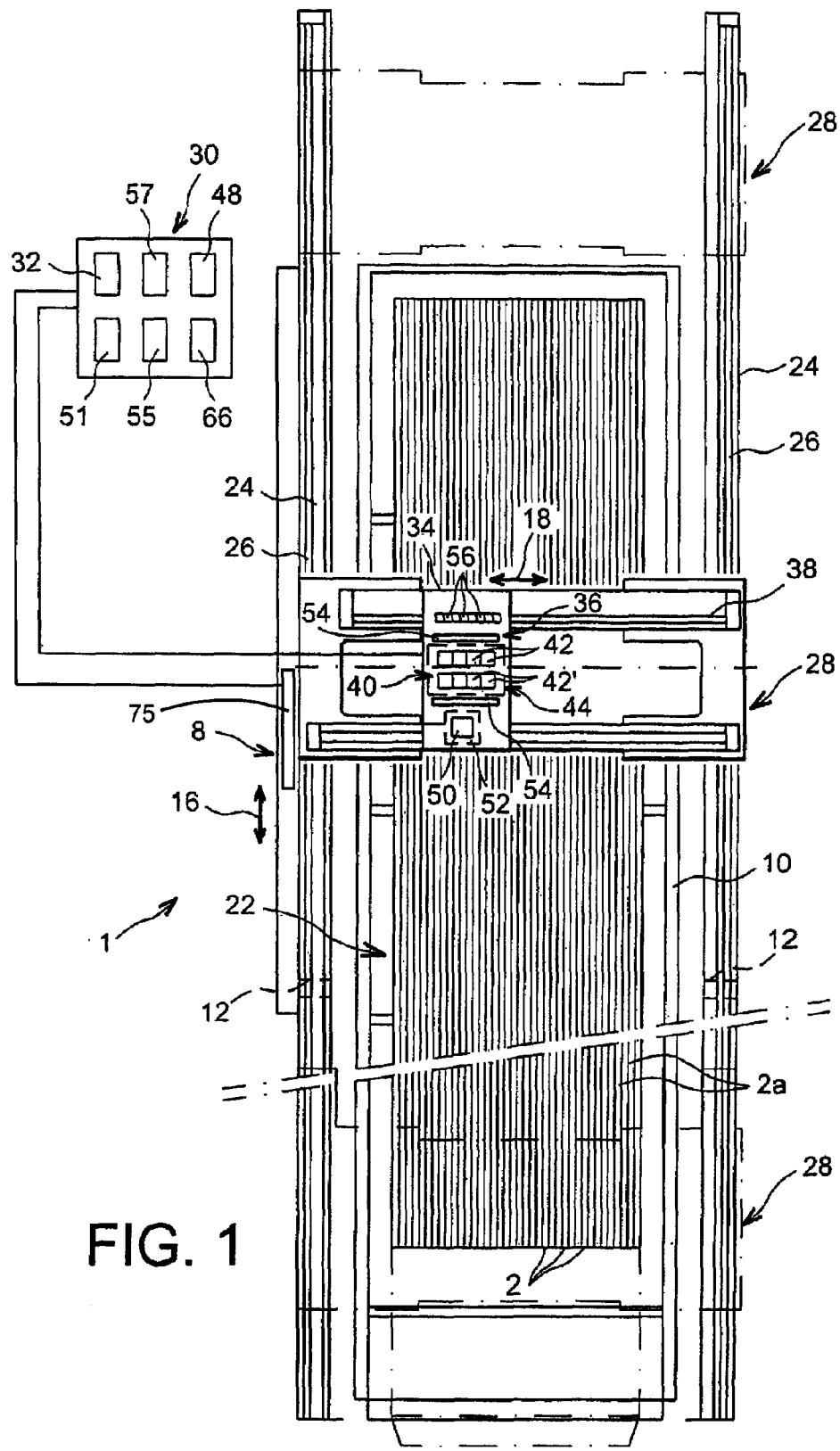
FIG. 1 represents a top view of a device for controlling the exterior aspect of fuel rods, according to a preferred embodiment of the present invention.
Figure 2:
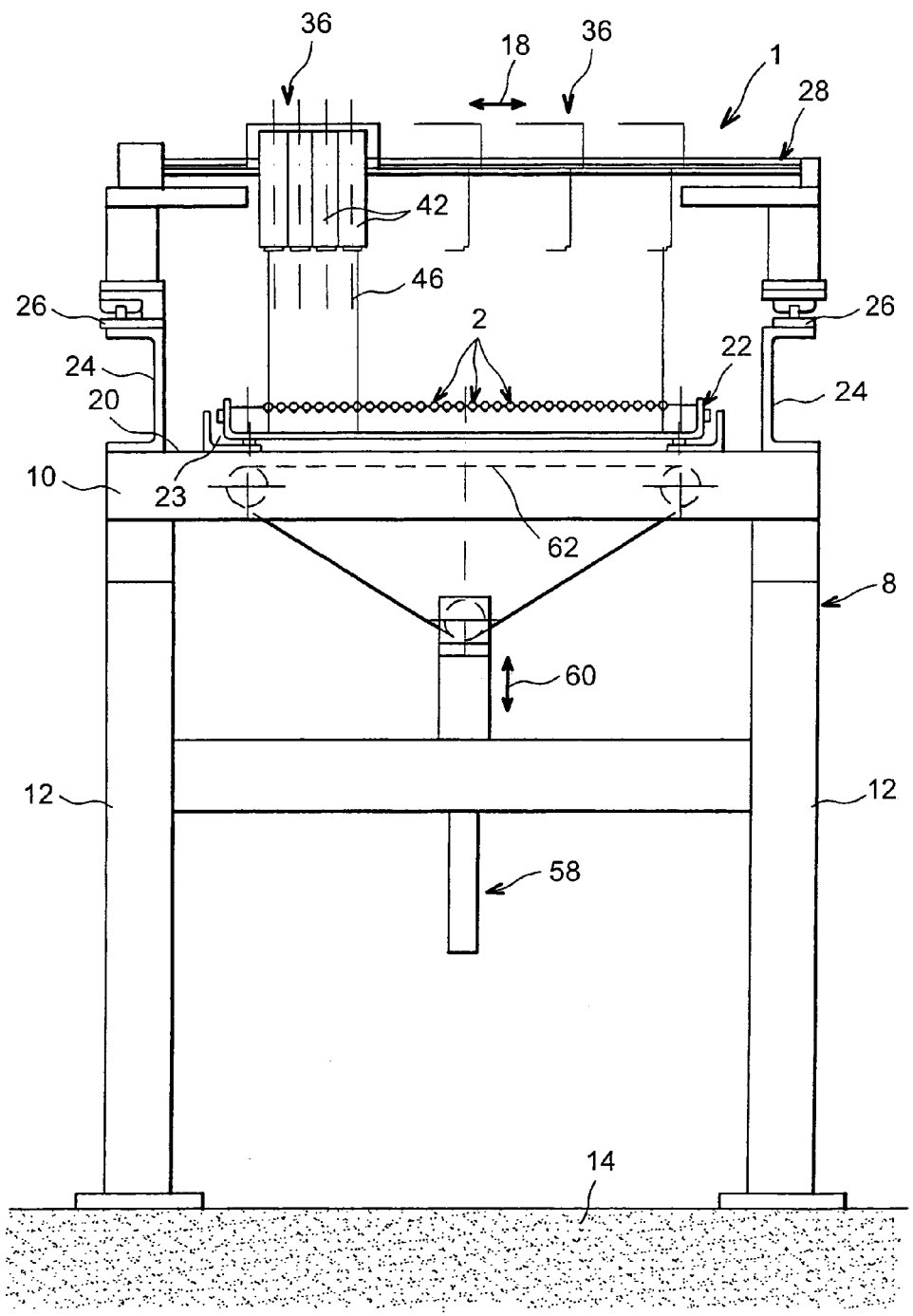
FIG. 2 represents a frontal view of the control device represented in FIG. 1, FIGS. 3a to 3c each represent a side view, on a larger scale, of a part of the control device represented in FIGS. 1 and 2, schematically showing various operations carried out during an exterior aspect control of fuel rods.

In reference both to FIGS. 1 and 2, a device 1 for controlling the exterior aspect of fuel rods 2 for nuclear reactors (not shown) according to a preferred embodiment of the present invention is represented.

It is pointed out that said device 1 is intended to allow the carrying out of an aspect control of the exterior surface 2a of the rods 2, at the end of the production cycle of said rods 2. Thus, the device 1 is designed in such a way as to verify the surface condition of the exterior surface 2a of the rods 2 and is therefore capable of detecting the presence of any unacceptable defects in respect of the necessary quality requirements, the searched for defects being the same types as those detailed above in the state of the prior art section.

Figure 3A:
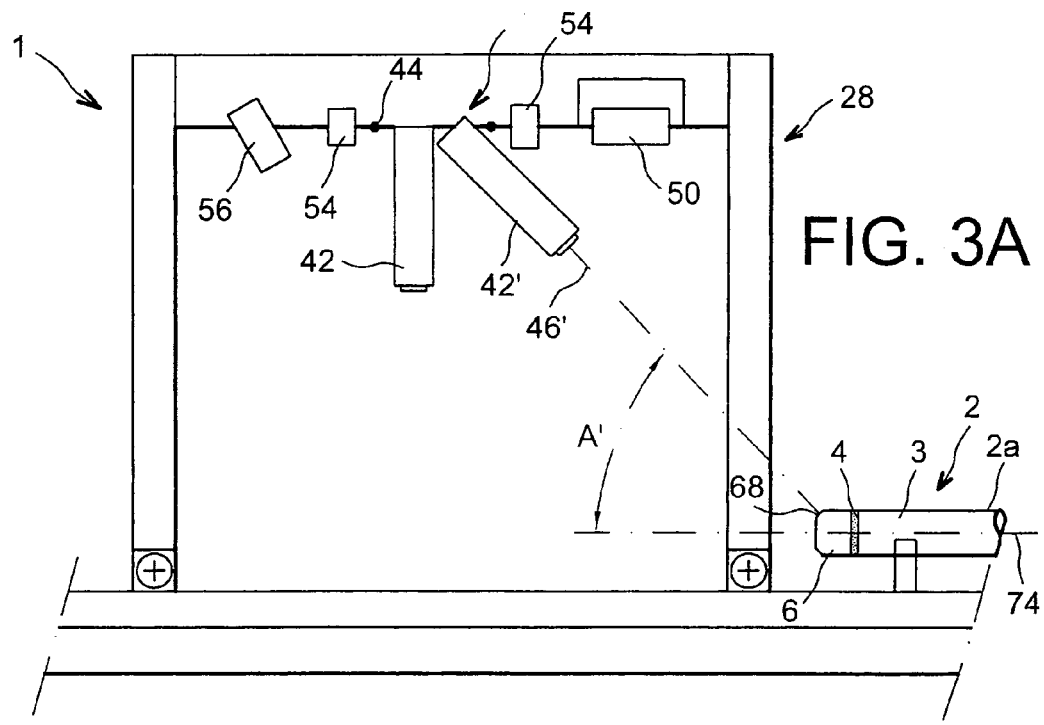

In this respect, it is pointed out that the expression "exterior surface 2a" of a rod 2 is understood to comprise the exterior surface of a principal cladding 3 of the rod 2, a weld bead 4 linking the principal cladding 3 to an end cap 6, and the exterior surface of said end cap 6, as is, notably, represented in FIG. 3a. It is pointed out that a truncated surface 68 of the end cap 6, normally called the end surface of the cap 6, forms an integral part of the exterior surface 2a of a rod 2.

In FIGS. 1 and 2, one can see that the device 1 comprises a displacement stand 8, said stand being essentially constituted of a frame 10 mounted on feet 12 fastened to the ground 14. The frame 10, of a substantially rectangular shape, preferentially lies parallel to the ground 14 and extends longitudinally along a longitudinal direction of the stand 8, represented by the double arrow 16 in FIG. 1, and transversally along a transversal direction of the stand 8, represented by the double arrow 18 in said figure.

Thus, the frame 10 of the displacement stand 8 defines a flat surface 20, substantially horizontal and parallel to the ground 14, on which may be placed a plate 22 equipped with a plurality of rods 2, said rods being arranged substantially parallel alongside each other. Moreover, the plate 22 on which the fuel rods 2 are lying at the end of their production cycle, for example in such a way as to form a bundle of thirty two elements, is brought to the stand 8 in such a way that said rods 2 are arranged parallel to the longitudinal direction 16 of the stand 8, and thus substantially parallel to the flat surface 20 of the frame 10. It is also pointed out that a rectangular position 23, specifically dimensioned to receive the plate 22, is provided at the level of the flat surface 20 of the frame 10. In this way, the plate 22 is capable of occupying a precise position in relation to the stand 8, said precise position being a key aspect in the proper unwinding of the operations of controlling the exterior aspect of the rods 2.

Furthermore, the displacement stand 8 of the device 1 comprises two beams 24 extending substantially parallel to the longitudinal direction 16 of the stand 8, and being located on either side of the rectangular position 23. On each of said beams 24 is placed a running rail 26 that enables the displacement of a trolley 28 parallel to the longitudinal direction 16 of the stand 8.

As can be seen in FIG. 1, the running rails 26 have a longer length than that of the plate 22, in order to allow the freeing of the trolley 28 and, as a result, to assure a good control of the truncated surface 68 of the end caps 6 of the fuel rods 2, as will be described hereafter.

The trolley 28 of the control device 1 is therefore capable of being displaced along the running rails 26 of the stand 8, preferentially by means of a step motor and a toothed belt (not shown), said motor being controlled by control means 32 forming an integral part of an electronic and computer assembly 30, the principal function of which lies in the total automation of the control device 1. Obviously, the assembly 30 may comprise conventional elements such as computers, multiplexers or even supply modules, which consequently will not be further described due to their commonplace nature for those skilled in the art. On the other hand, the elements of the assembly 30 specific to the present invention will naturally be described hereafter.

The displacement stand 8 is equipped with a coding ruler 75 (see FIG. 1) that makes it possible to deliver, to the electronic and computer assembly 30, preferably continuously, the position of the trolley 28 in relation to said displacement stand 8.

A support 34 for an inspection and measurement head 36 is mounted on the trolley 28 of the device 1, as is clearly illustrated in FIGS. 1 and 2. In said figures, one can indeed see that the support 34 is lying on the running rails 38 extending substantially parallel to the transversal direction 18 of the stand 8, in such a way that said support 34 is then capable of being displaced parallel to this same direction, in relation to the trolley 28.

With this specific arrangement and by carrying out judicious displacements of the support 34 in relation to the trolley 28 and of said trolley 28 in relation to the displacement stand 8, it is therefore obvious that the inspection and measurement head 36 is capable of covering the totality of the upper surface formed by the rods 2 lying in bundles of thirty two elements on the plate 22.

Here again, it is pointed out that the displacement of the support 34 on the trolley 28 is preferentially carried out by means of a step motor and a toothed belt (not shown), said motor preferably being controlled by the control means 32 of the electronic and computer assembly 30.

The inspection and measurement head 36, integral with the support 34, comprises optical means 40 that preferentially take the form of a plurality of charge coupled device cameras 42, 42'. In the preferred embodiment described and represented in FIGS. 1 and 2, the optical means 40 comprise four primary cameras 42 and four secondary cameras 42'. Moreover, it is pointed out that said secondary cameras 42' are intended to scan the truncated surface 68 of the end caps 6 of the rods 2, whereas the primary cameras 42 are intended to scan the whole of the exterior surface 2a of said rods 2, apart from said truncated surface 68 of the end caps 6. In this respect, it is pointed out that the surface inspected by the primary cameras 42 is substantially cylindrical and of circular section.

Preferably, the group of primary cameras 42 and the group of secondary cameras 42' are each in the form of a row of cameras parallel to the transversal direction 18, and are each intended to scan eight adjacent rods 2 at the same time. Moreover, each of said cameras 42, 42' is effectively adjusted to have two adjacent rods 2 in its field of view. Obviously, the number of cameras 42, 42' and the number of rods 2 that they are capable of scanning at any single time may be adapted as a function of the needs encountered, without going beyond the scope of the invention.

The four primary cameras 42, of the progressive scan type, are preferably mounted on a plate 44 assembled on the support 34, in such a way that each optical axis 46 of a camera 42 is located substantially perpendicular to the two rods 2 that it has in its field of view, and substantially perpendicular to the flat surface 20 of the frame 10, as is clearly shown in FIG. 2.

Moreover, the four secondary cameras 42' are preferably also mounted on said plate 44, but in such a way as to be capable of correctly viewing the truncated surface 68 of the end caps 6. Thus, as is clearly shown in FIG. 3a, the primary cameras 42 are mounted substantially vertically, whereas the secondary cameras 42' are mounted at an angle.

The cameras 42, 42' are capable of delivering images of the rods 2 to an image acquisition and processing system 48 to which they are linked, the two dimension processing software type system 48 forming an integral part of the electronic and computer assembly 30.

Consequently, the system 48 is capable of detecting defects present on the fuel rods 2, such as geometric defects similar to those indicated above in the state of the prior art section, from images delivered by the cameras 42, 42' and following a conventional processing of said images. Naturally, the image acquisition and processing system 48 is also capable of detecting cleanliness defects such as the presence of traces of oil and foreign bodies on the exterior surface 2a of a rod 2, or even the presence on said surface 2a of black or coloured marks of surface area greater than a determined value.

In addition, the system 48 is further capable of detecting all of the weld aspect defects of the end cap 6, such as pitting, blisters, cracking, overflows, shortages, sags or even colouring defects in the weld bead 4.

The inspection and measurement head 36 also comprises a roughness tester 50, mounted on a lifting plate 52 assembled on the support 34, in such a way that said roughness tester 50 is located substantially at the level of the support 34 when the lifting plate 52 occupies a retracted position, and in such a way that said roughness tester is located near to the rods 2 when the plate 52 is in a projecting position. It should be noted that this latter position is that adopted to carry out a measurement of the depth of a geometric defect detected by the system 48, and that this same projecting position is obtained by a displacement towards the floor 14 of the lifting plate 52, in a substantially perpendicular direction to the flat surface 20 of the frame 10.

In this respect, the displacements of the lifting plate 52 are preferentially assured by the control means 32 of the assembly 30.

Typically, the roughness tester 50 that assures the measurement of the depth of geometric defects detected is a PERTHOMETER (registered trade name) or CONFOCAL (registered trade name) type optical sensor roughness tester, in which the range of measurement is plus or minus 300μ.

In addition, it is pointed out that the data collected by the roughness tester 50 is transmitted to the acquisition and processing means 51 forming an integral part of the assembly 30, said means 51 then being capable of processing the data received in order to determine the depth of the defects detected, then transferring the depth measurements to a central memory 55 of said assembly 30.

More specifically in reference to FIG. 1, the head 36 comprises lighting ramps 54, preferably assuring a continuous and stable lighting. By way of illustrative example, two ramps 54 may be placed parallel to the transversal direction 18 of the stand 8, respectively on either side of the optical means 40.

Apart from the faculty that the ramps 54 offer to the cameras 42, 42' to take good quality images, said ramps 54 may also be placed in association with diode detectors 56, integral with the support 34. This association allows the detection of cleanliness defects present on the exterior surface 2a of the rods 2, such as traces of oil, as will be described in more detail hereafter. Thus, said diode detectors 56 may, if necessary, be used to detect traces of oil that are difficult to detect with the aid of the optical means 40 described above and coupled to the image acquisition and processing system 48.

Preferably, each diode detector 56, arranged in such a way as to be able to be positioned plumb with a fuel rod 2 on the support 34, is equipped with a lens focusing its measurement field on the rod 2 concerned, and is capable of receiving the light emitted by the lighting ramps 54 and reflected on the exterior surface 2a of said rod 2. In addition, the detectors 56 are linked to a management module 57 forming an integral part of the assembly 30, and enabling in particular the acquisition of the "ALL" or "NOTHING" results delivered by the detectors 56.

By way of indicative example, in the preferred embodiment of the present invention, the detectors 56 are placed alongside each other in such a way as to form a row extending substantially parallel to the lighting ramps 54, and thus substantially parallel to the transversal direction of the stand 8.

More specifically in reference to FIG. 2, it can be seen that the control device 1 further comprises means of rotating 58 the rods 2, said means 58 preferably being assembled on the feet 12 of the device 1.

The means 58 are vertically telescopic, in other words they can be displaced in relation to the stand 8 along a vertical direction represented by the double arrow 60 in FIG. 2, said vertical direction thus being perpendicular to the flat surface 20 of the frame 10. In this way, by bringing into action a step motor (not shown), preferentially controlled by the control means 32, it is possible to establish or to break the contact between the drive belts 62 of the means 58 and the means (not shown) themselves located in permanent contact with the lower part of the exterior surface 2a of the rods 2. It is pointed out that in FIG. 2, a single drive belt 62 is visible, due to the fact that the specific plan of this FIG. 2 implies that the other belts are hidden by the one shown. However, the drive belts 62, preferably identical, are spaced from each other along the longitudinal direction 16, for example around every 400 mm.

Furthermore, the drive belts 62 are capable of being brought into movement by means of a step motor (not shown), again preferentially controlled by the control means 32, so that the upper part of said belts 62 can be displaced in a direction substantially parallel to the transversal direction 18 of the stand 8.

In this respect, it is pointed out that in a manner known to those skilled in the art but not represented, the rods 2 may be displaced by means 58 in such a way that they lie on landings on which are integrated rollers, said rollers being capable of being driven by the drive belts 62. In addition, the plate 22 is pierced in order to be able to be crossed by said drive belts 62, and thus to allow the contact between these and the rollers supporting the rods 2.

Thus, when the drive belts 62 are actually brought into movement and are in contact with the rollers supporting the rods 2, they then provoke the rotation of all of said rods 2 along their own longitudinal axes.

In this way, it is possible to control all of the exterior surface 2a of each rod 2 by means of the inspection and measurement head 36, by carrying out a plurality of backward and forward movements with the trolley 28, each backward and forward movement of the trolley 28 being carried out along the whole length of the rods 2 to be controlled, for a given angular portion of said rods 2.

It is pointed out that during the delivery of an image by the optical means 40 to the image acquisition and processing system 48, the electronic and computer assembly 30 is capable of associating with said image an address indicating the angular position of the rod 2 concerned, and the position of the trolley 28 in relation to the displacement stand 8, said position being delivered by the coding ruler 75 as mentioned above. In addition, the images processed by the system 48, for which one or several defects have been detected, are capable of being transferred into the central memory 55 of the assembly 30, while being associated with their respective addresses, the content of which is detailed above.

Finally, the assembly 30 of the device 1 comprises information means 66 capable of delivering and/or memory storing, for each rod 2 controlled, a result file of the control carried out. As will be more fully explained hereafter, said result file may indicate "pass", "fail" or "to be recontrolled", as well as the address and/or the image of the defect(s) detected in the two latter cases.

The device 1 for controlling the exterior aspect that has just been described is capable of operating in the preferred manner described below, referring in particular to FIGS. 3a to 3c and to FIG. 4.

In the first instance, in referring to FIGS. 3a to 3c, the operation of the device 1 will be described, during the exterior aspect control operations aiming to detect geometric defects, such as defects that could take the form of longitudinal or circumferential grooves on the exterior surface 2a of the rods 2, it being possible to consider said grooves as defects when they attain a depth greater than 25μ. In addition, they may also involve impacts, caulking or even stripping off of material, still at the level of said exterior surface 2a of the rods 2.

A plate 22 of thirty two rods 2 is first transported in the direction of the displacement stand 8, for example in an automatic manner, in order to be brought to the rectangular position 23 provided for this purpose on the frame 10.

In a known manner, the means of rotating 58 are then brought into action by the control means 32, in order to free the rods from their arrival position, in such a way that they then lie on their associated rollers.

At this moment, the trolley 28 occupies a start position in which it is rested against the stand 8 and situated completely beyond the rods 2 in the longitudinal direction 16, as shown by a dotted line in FIG. 1. In addition, the support 34 for the inspection and measurement head 36 is positioned on the trolley 28 in such a way that said head 36 can inspect the first eight rods 2, located at the end of the bundle of thirty two elements.

As shown in FIG. 3*a*, when the trolley 28 occupies its start position, the optical axes 46' of the inclined secondary cameras 42' are substantially perpendicular to the truncated surface 68 of the end cap 6, said truncated surface 68 normally being called the end surface of the cap 6 and forming an integral part of the exterior surface of said cap 6. In addition, the truncated surface 68 has a principal axis identical to a longitudinal axis 74 of the rod 2. By way of illustrative example, the optical axes 46' of the secondary cameras 42' may be inclined 450 in relation to a horizontal plane parallel to the flat surface 20 of the frame 10. In other words, the optical axes 46' form an angle A' of around 45° with the longitudinal axis 74 of the rods 2, in a plane perpendicular to the ground 14.

An image is then taken by each of the four secondary cameras 42', then transmitted to the image acquisition and processing system 48, which, as soon as the images are received, begins to carry out the processing. It should be noted that in the preferred embodiment described, each image taken by a secondary camera 42' contains the representation of a part of two truncated end surfaces 68 belonging respectively to two adjacent rods 2.

In parallel, the control means 32 displace the trolley 28 facing the end cap 6 in order to begin the scanning of the remainder of the exterior surface of said end cap 6, and that of the cladding 3 and the weld bead 4 of the rods 2. In this respect, it is pointed out that the part of the exterior surface of the end cap 6 remaining to be inspected is substantially cylindrical and of circular section, and constitutes an extension of the exterior surface of the cladding 3.

Figure 3B:
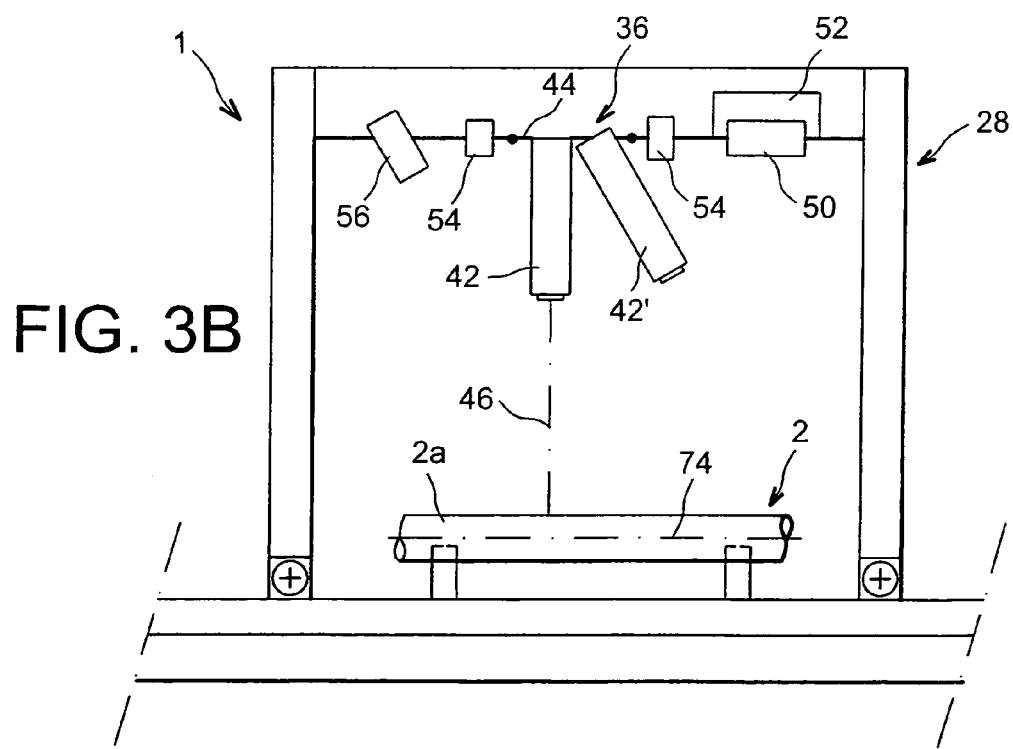

To do this, the trolley 28 is displaced on the running rails 26, along the whole length of the rods 2, as shown schematically in FIG. 3*b*. Images are then taken regularly by the primary cameras 42, for precise positions of the trolley 28 in relation to the stand 8, so that the upper part of the exterior surfaces 2*a* of the rods 2, visible by said same primary cameras 42, are completely scanned. In this respect, it is pointed out that the precision of the positions of the trolley 28 is easily assured by the coding ruler 75 equipping the displacement stand 8.

After each image is taken, the images are directly delivered to the system 48, then analysed by said system 48 while the trolley 28 is displaced in order to return to the position in which the primary cameras have to take the following images.

In the event where one or several geometric defects are detected by the system 48, the corresponding images are transferred into the central memory 55, while being associated with their respective addresses indicating the angular-position of the rod 2 concerned, and the position of the trolley 28 in relation to the displacement stand 8. On the other hand, the images that have not been the subject of any detection of geometric defect are preferably not conserved in the memory. Nevertheless, it could be provided that they are stored for a given time, for example of the order of several days, by storing them in a compressed manner on a recording support such as a CD-ROM.

Thus, the trolley 28 is displaced at constant speed by the control means 32 up to its final position in which it rests against the stand 8, and located facing the ends of the rods 2 opposite the caps 6, as also shown by a dotted line in FIG. 1.

Once this final position has been attained, the control means 32 provoke the bringing into action of the means of rotating 58 the rods 2, so that the eight rods 2 inspected are pivoted along their own longitudinal axes. The fuel rods 2 concerned are consequently positioned in a different angular position from the previous one, with the aim of controlling another angular section of the exterior surface 2*a* of said rods 2.

When the rotation has taken place, the scanning of the exterior surfaces of the claddings 3 and the caps 6 and the scanning of the weld beads 4 is carried out again, during the displacement of the trolley 28 from the final position to the start position. In the same way as previously, the images taken by the primary 42 and secondary 42' cameras having been the subject of a detection of at least one geometric defect are stored in the central memory 55.

By way of illustrative example, the means of rotating 58 are programmed so that the exterior surface 2*a* of the rods 2 is entirely scanned following twelve rotations. In such a case, the trolley 28 is controlled by the control means 32 in such a way as to carry out six backward and forward movements above said adjacent eight rods 2, each backward and forward movement corresponding to a given angular position of said rods 2.

Once all of the backward and forward movements have been carried out by the trolley 28 and the images of the geometric defects have been transferred to the central memory 55 of the assembly 30, the control means 32 generate displacements of the roughness tester 50 with the aim of measuring the depth of each of the geometric defects detected.

Thus, for each geometric defect detected, the trolley 28, the support 34 and the means of rotating 58 and controlled by the control means 32, so that the roughness tester 50 is placed facing the geometric defect concerned. Obviously, said displacements are carried out as a function of the address of the stored image containing the defect, and as a function of the positioning of said defect on the image.

Figure 3C:
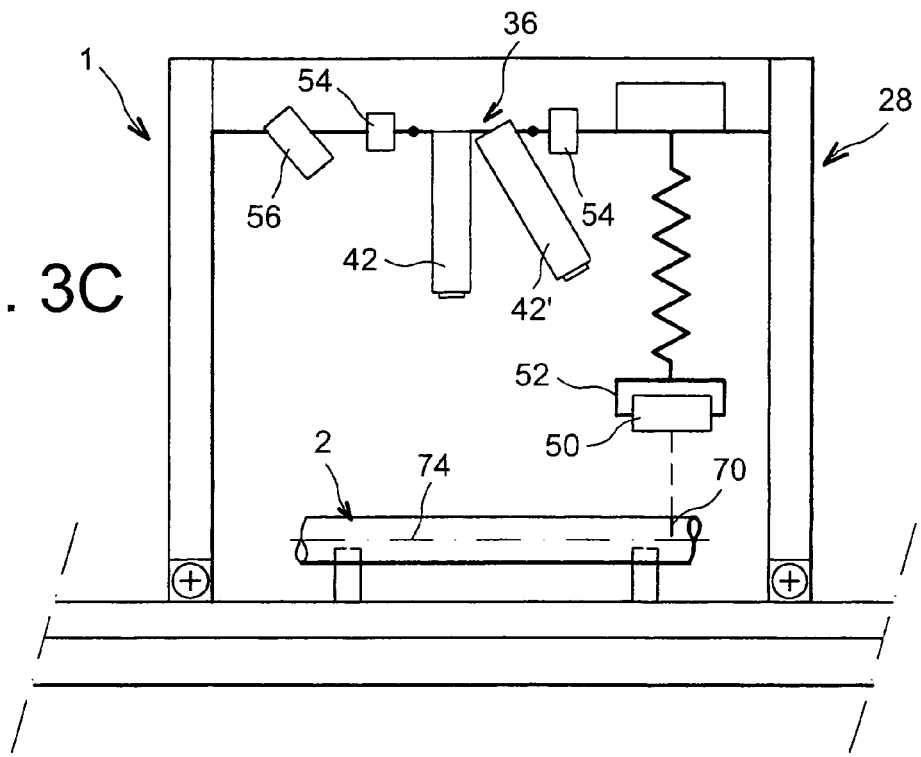

Then, the control means 32 provoke the displacement of the lifting plate 52, in such a way that the roughness tester 50 is placed near to the defect 70 detected, as shown in FIG. 3*c*. By way of indicative example, the plate 52 is displaced vertically downwards in such a way that the roughness tester 50 is placed 10 mm from the defect 70 detected.

Measurements are then carried out by said roughness tester 50, which directly transmits the data collected to the acquisition and processing means 51 so that they can determine the depth of the defect 70.

This operation is therefore repeated as many times as necessary to measure the depth of all of the geometric defects, the depth values then being associated with the images in the central memory 55 of the assembly 30.

The control of the first eight rods 2 with regard to geometric defects now being completed, the trolley 28 is then displaced in its start position such as described here above, then the support 34 is also displaced in relation to the trolley 28 in such a way that the head 36 can inspect the next eight rods 2, as is shown in fine lines in FIG. 2.

All of the operations described below are carried out in the same way for said eight new rods 2, as well as for the two other remaining sets of eight adjacent rods 2.

Again by way of illustrative example, another solution could consist in providing that the trolley 28 is controlled by the control means 32 in such a way that, following the inspection of the first angular section of the first set of eight adjacent rods 2, said trolley 28 does not inspect the second angular section of the first set, but said first angular section of the second set of eight adjacent rods 2.

Consequently, contrary to the example described previously, the trolley 28 carries out a succession of backward and forward movements in order to inspect a same angular section of each of the thirty two rods 2 in the bundle. Once said angular section has been fully inspected, the control means 32 provoke the bringing into action of the means of rotating 58 the rods 2, which then leads to a pivoting of all of said rods 2 in such a way that their next angular section can in turn be controlled by the trolley 28.

In addition, it could be provided that, during the backward and forward movements carried out by the trolley 28 and as soon as a geometric defect has been detected, the control means 32 immediately generate a displacement of the roughness tester 50, with the aim of measuring the depth of said detected geometric defect.

Whatever the solutions retained among those detailed above, when the bundle of rods 2 is inspected, the trolley 28 is equipped with a reader (not shown) integral with the support 34, which is capable of reading a bar code (not shown) present on each of said rods 2.

Thus, when the reader reads a bar code, all of the information known on the rod 2 concerned is transferred to the information means 66 capable of delivering and/or memory storing a result file of the control carried out.

Said result file, presenting the bar code of the rod 2, could firstly indicate "pass" when no geometric defect has been detected by the image acquisition and processing system 48.

Moreover, in the event where at least one geometric defect has been detected by the system 48, the result file then preferably indicates "fail". In this case, said file may also advantageously comprise the images of the detected defects, associated with the respective addresses and the associated depth values.

It is pointed out that in the event where no geometric defect detected exceeds a pre-established depth value, for example 25µ, the result file could then indicate "to be recontrolled", in order to determine if the presence of the defects adversely affects or not, in a significant manner, the quality of the surface condition of the rod 2.

The detection operations of certain cleanliness defects such as the presence of traces of oil and foreign bodies on the exterior surface 2a of the rods 2, or even the presence on said surface 2a of black or coloured marks with a surface area greater than a determined value, may be carried out in a similar manner to that detailed for the geometric defect detection operations, and simultaneously with these latter operations, as with operations for detecting aspect defects in the weld bead 4 of the end cap 6, said defects can be present in the form of pitting, blisters, cracking, overflows, shortages, sags or even colouring defects in the weld bead.

Indeed, when the images are delivered by the primary 42 and secondary 42' cameras to the image acquisition and processing system 48, it is capable of differentiating geometric defects from cleanliness or weld bead aspect defects. Thus, when a cleanliness or weld bead 4 aspect defect is detected, the image associated with its address is directly transferred to the central memory 55, but the measurement operation with the aid of the roughness tester 50 will obviously not be ordered.

In this way, following the reading of the bar code of a rod 2, the information known on said rod 2 and transferred to the means of information 66 may then include data concerning cleanliness or weld bead 4 aspect defects of the type described above, in such a way that in such a case, the result file of the control must indicate "fail".

In the event where the association between the cameras 42, 42' and the image acquisition and processing system 48 do not prove sufficiently satisfactory for the detection of cleanliness defects of the type of oil traces present on the exterior surface 2a of the rods 2, it is then possible to carry out a detection of this type of defect by means of the lighting ramps 54 coupled to the diode detectors 56.

Obviously, the detection by means of said lighting ramps 54 is carried out in parallel to the abovementioned operations, using the cameras 42, 42'.

Figure 4:
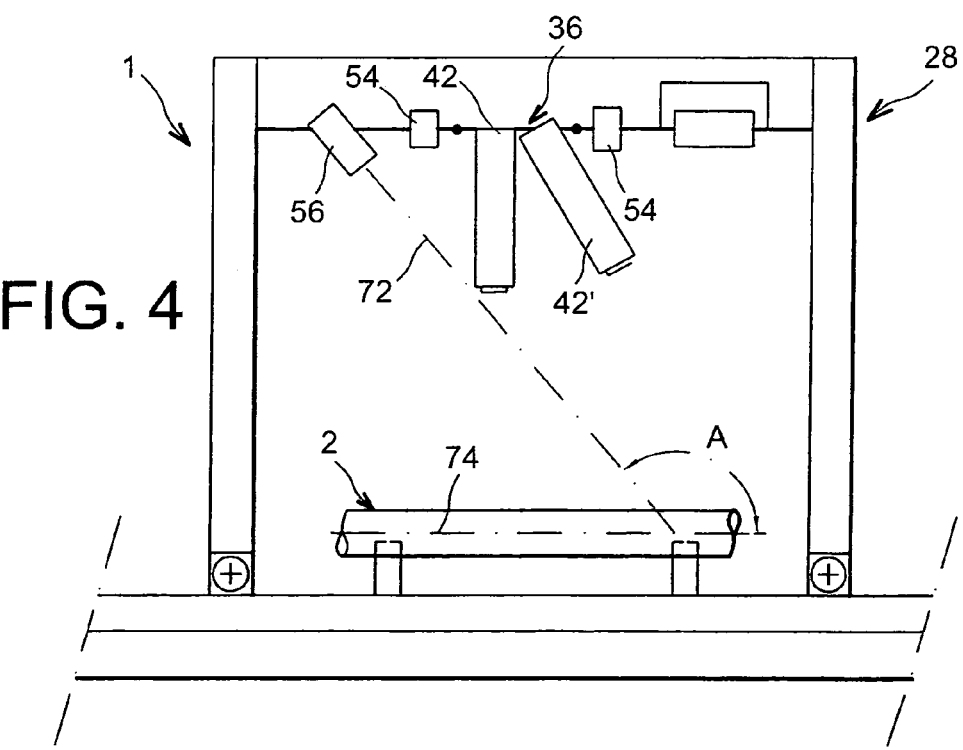
FIG. 4 represents a side view, on a larger scale, of a part of the control device represented in FIGS. 1 and 2, schematically showing an operation of detecting traces of oil on the fuel rods.

Thus, as shown in FIG. 4, during the displacement of the trolley 28 described above, the detectors 56 receive the light reflected on the rods 2 and emitted by the ramps 54. To do this, the optical axes 72 of the detectors 56 preferentially form an angle A of around 60° with the longitudinal axis 74 of the rods 2, in a plane perpendicular to the ground 14.

Preferably, at the same time as the images are taken by the primary 42 and secondary 42' cameras, the management module 57 acquires the results "ALL" or "NOTHING" delivered by said detectors 56.

Consequently, when a detector 56 has in its field of view a trace of oil adhering to the exterior surface 2a of a rod 2, the reflection is then more intense and the signal delivered by the detector 56 goes from "NOTHING" to "ALL". In this way, during the following acquisition carried out by the management module 57, said module 57 is informed of the presence of a trace of oil at a given address, and may therefore transfer said information to the central memory 55.

Naturally, after each acquisition of the management module 57, it provokes the return to zero of the signals generated by the diode detectors 56.

Thus, once again, following the reading of the bar code of a rod 2, the information known on said rod 2 and transferred to the information means 66 may then include data concerning cleanliness defects of the trace of oil type, in such a way that in this case, the result file of the control must indicate "fail".

Moreover, it is pointed out that with the presence of the cameras 42, 42' and the image acquisition and processing system 48 and, more specifically, with that of the primary cameras 42, it is possible to verify that each rod 2 has indeed made a complete rotation during the defect detection operations.

Indeed, each rod 2 has an identification number inscribed several times on the exterior surface of the cladding 3, for example four times. Said four identical identification numbers are thus inscribed on a same longitudinal level of the rod 2 concerned, for example of the exterior surface of the cladding 3 near to the end cap 6, parallel to their longitudinal axis 74, and every 90° around said axis.

In this way, during the first forward movement of the trolley 28, when it comes to be positioned at the specific level of the rods 2 where said identification numbers are inscribed, the primary camera 42 concerned takes an image placed in the memory of the central memory 55. On the image obtained, the specific position of the visible identification number then defines an angular start position of the rods 2.

Thus, the twelve angular control positions of the rod 2 being organised to overlap, the comparison between the first image and the twelfth image, theoretically identical, make it possible to determine if the rod 2 has undergone or not a complete rotation. If this is not the case, one or several additional increments may be ordered in order to inspect all of the exterior surface 2a of the rod 2.

Naturally, said comparison of the first and the final images taken by the primary camera 42 is carried out by means of the image acquisition and processing system 48.

The invention also concerns a method for controlling the exterior aspect of fuel rods 2 for nuclear reactors, said method being capable of being implemented with the aid of the control device 1 that has just been described, and comprising the principal steps consisting in detecting the geometric defects present on each rod 2 to be controlled, with the aid of optical means 40 having at least one camera 42, 42' and linked to the image acquisition and processing system 48, then measuring the depth of each geometric defect detected during the geometric defect detection step, with the aid of a roughness tester 50.

Obviously, various modifications may be made by those skilled in the art to the device 1 and the exterior aspect control method that have been described here above, uniquely by way of example and in a non-limitative manner.

The invention claimed is:

1. Device (1) for automatically controlling an exterior aspect of a plurality of fuel rods (2) for nuclear reactors, characterised in that it comprises optical means (40) comprising a plurality of primary cameras (42) and a plurality of secondary cameras (42'), said secondary cameras being inclined with respect to said primary cameras in order to be able to scan a truncated surface (68) of an end cap (6) of each of the fuel rods (2) to be controlled, and further comprises an electronic and computer assembly (30) comprising means for acquiring an image and processing (48) the image and linking the plurality of primary cameras (42) and the plurality of secondary cameras (42') to the electronic and computer assembly (30) and delivering the images of the plurality of fuel rods (2) to the electronic and computer assembly (30) and detecting geometric defects present on each rod (2) to be controlled, and in that the device (1) further comprises a roughness tester (50) and means for automatically controlling the roughness tester (50), the roughness tester (50) further comprising means for automatically measuring a depth of each geometric defect detected by the electronic and computer assembly (30).

2. Aspect control device (1) according to claim 1, characterised in that it comprises:
    a displacement stand (8),
    a platform (22) placed on the displacement stand (8), said platform (22) being adapted to be equipped with said plurality of fuel rods (2) arranged substantially parallel alongside each other, so that the rods (2) are laid out parallel to a longitudinal direction (16) of said stand (8),
    a trolley (28) comprising means for selectively displacing the trolley (28) along a first axis parallel to the longitudinal direction (16) of said displacement stand (8),
    an inspection and measurement head support (34) mounted on said trolley (28) and comprising means for selectively displacing the inspection and measurement head support (34) along a second axis in relation to said trolley parallel to a transversal direction (18) of said displacement stand (8),
    means for controlling (32) operatively connected to the electronic and computer assembly (30), the means for controlling (32) comprising means for automatically displacing the trolley along the first axis and to automatically displace the inspection and measurement head support (34) along the second axis,
    an inspection and measurement head (36), the inspection and measurement head (36) having at least the optical means (40), and the roughness tester (50),
    means (58) for automatically rotating the fuel rods (2) along their own longitudinal axes (74) to produce multiple angular positions of said rod (2), and
    a coding ruler (75) provided on the displacement stand (8) comprising means for automatically delivering to the electronic and computer assembly (30) the position of the trolley (28) along the first axis in relation to said stand (8).

3. Aspect control device (1) according to claim 2, characterised in that for each rod (2), the optical means (40) comprises means for automatically scanning an exterior surface (2a) of each rod (2) by a plurality of displacements of the trolley (28) along the whole rod (2) concerned, each displacement being carried out for each angular position of said rod (2).

4. Aspect control device (1) according to claim 3, characterised in that the optical means (40) comprises means for automatically delivering a plurality of images to the electronic and computer assembly (30), each image delivered from the rod (2) being associated with an address indicating an angular position of said rod (2) and the position of the trolley (28) along the first axis in relation to the displacement stand (8).

5. Aspect control device (1) according to claim 4, characterised in that the electronic and computer assembly (30) comprises means for provoking a displacement of the roughness tester (50) along a third axis that is transverse to the first axis, thanks to the addresses associated with the images delivered by the optical means (40).

6. Aspect control device (1) according to claim 2, characterised in that the inspection and measurement head support (34) comprises a plate (44), said primary cameras (42) and said secondary cameras (42') being mounted on the plate (44), the inspection and measurement head support (34) further comprising means for selectively displacing the inspection and measurement head support (34) along at least one axis, said primary (42) and secondary (42') cameras being cameras with a charge coupled device and each camera comprising means for simultaneously scanning at least two adjacent fuel rods (2).

7. Aspect control device (1) according to claim 2, characterised in that aspect control device (1) further comprises a lifting plate (52), the roughness tester (50) being mounted on the lifting plate (52), the lifting plate (52) further comprising means for selectively displacing the lifting plate (52) along a third axis that is transverse to the first axis and assembled on said inspection and measurement head support (34) so that the roughness tester (50) is closer to each rod (2) to carry out the measurement of the depth of each geometric defect detected.

8. Aspect control device (1) according to claim 2, characterised in that the inspection and measurement head (34) further comprises diode detectors (56) and lighting ramps (54) that make it possible to detect cleanliness defects present on each fuel rod (2) to be controlled.

9. Aspect control device (1) according to claim 2, characterised in that the electronic and computer assembly (30) comprises means for automatically delivering a memory and means for automatically storing the memory in the form of a result file of the said depth of each geometric defect and the said position of the trolley (28) along the first axis in relation to the displacement stand (8).

* * * * *